United States Patent [19]

Yoon

[11] Patent Number: 5,470,873

[45] Date of Patent: * Nov. 28, 1995

[54] DIABETES PREVENTION AND TREATMENT USING GAMMA-PYRONES

[75] Inventor: Ji-Won Yoon, Calgary, Canada

[73] Assignee: University Technologies International, Inc., Calgary, Canada

[*] Notice: The portion of the term of this patent subsequent to Mar. 29, 2011, has been disclaimed.

[21] Appl. No.: 179,555

[22] Filed: Jan. 10, 1994

Related U.S. Application Data

[63] Continuation-in-part of Ser. No. 978,958, Nov. 23, 1992, Pat. No. 5,298,525.

[51] Int. Cl.$^6$ .......................... A61K 31/35; A61K 35/78
[52] U.S. Cl. ..................... 514/460; 514/866; 424/195.1
[58] Field of Search ................................. 514/460, 866; 424/195.1

[56] References Cited

U.S. PATENT DOCUMENTS

| | | | |
|---|---|---|---|
| 3,799,945 | 3/1974 | D'Amico et al. | 260/345.9 |
| 4,276,890 | 7/1981 | Fichera | 131/270 |
| 4,311,691 | 1/1982 | Fichera | 424/48 |
| 4,575,502 | 3/1986 | Hider et al. | 514/184 |
| 4,665,064 | 5/1987 | Hider et al. | 514/184 |
| 4,666,927 | 5/1987 | Hider et al. | 514/350 |
| 4,738,975 | 4/1988 | Nohara et al. | 514/338 |
| 4,840,958 | 6/1989 | Hider et al. | 514/332 |
| 4,912,118 | 3/1990 | Hider et al. | 514/292 |
| 4,989,870 | 2/1990 | Narutomi et al. | 514/348 |
| 5,158,966 | 10/1992 | Lafferty et al. | 514/369 |

FOREIGN PATENT DOCUMENTS

| | | |
|---|---|---|
| 0159917A2 | 10/1985 | European Pat. Off. . |
| 2242191 | 8/1991 | United Kingdom . |
| WO87/07893 | 12/1987 | WIPO . |
| WO91/17751 | 11/1991 | WIPO . |

OTHER PUBLICATIONS

Amano, K., et al., Studies on autoimmunity for initiation of B-cell destruction: V: Decrease of macrophage-dependent T lymphocytes and natural killer cytotoxicity in Silica-treated BB rats. Diabetes 39: 590–596, 1990.

Asayama, K., et al., Alloxan-induced free-radical production in isolated cells: Selective effect on islet cells. Diabetes 33: 1008–1011, 1984.

Asayama, K., et al., Chemiluminescence as an index of drug-induced free radical production in pancreatic islets. Diabetes 33: 160–163, 1984.

Bach, J. F., Mechanisms of autoimmunity in insulin-dependent diabetes mellitus. Clin. Exp. Immunol. 72: 1–8, 1988.

Baek, H. S., et al., Direct involvement of macrophages in destruction of β-cells leading to development of diabetes in virus-infected mice. Diabetes 40: 1586–1597, 1991.

Baek, H. S., et al., Role of macrophages in the pathogenesis of encephalomyocarditis virus-induced diabetes in mice. J. Virology 64: 5708–5715, 1990.

Barrand, M. A., et al., Effects of the pyrones, maltol and ethyl maltol, on iron absorption from the rat small intestine. J. Pharm. Pharmacol. 39: 203–211, 1987.

Bertholf, R., et al., A long-term intravenous Model of aluminum maltol toxicity in rabbits: Tissue distribution, hepatic, renal, and neuronal cytoskeletal changes associated with systemic exposure. Toxicology and App. Pharmacology 98: 58–74, 1989.

Bhathal, P. S., et al., Chronic active hepatitis in mice induced by 3-hydroxy-4-pyrone. Experientia 40: 894–896, 1984.

Brennan, T. M., et al., A novel synthesis of maltol and related γ-pyrones. Tetrahedron Letters, 331–333, 1978.

Brismar, T., Neuropathy-Functional Abnormalities in the BB Rat. Metabolism 32: 112–117, 1983.

Brogren, C.–H. BB wistar rat monoclonal autoantibodies. Metabolism 32: Abstracts 165, 1983.

Brown, D. M., et al., Glomerular Manifestations of Diabetes in the BB Rat. Metabolism 32: 131–135, 1983.

Brownscheidle, C. M., et al., The Effects of Maternal Diabetes on Fetal Maturation and Neonatal Health. Metabolism 32: 148–155, 1983.

Cahill, G. F., et al., Insulin-dependent diabetes mellitus: the initial lesion, N. Eng. J. Med. 304: 1454–1455, 1981.

Chawla, R. K., et al., A new synthesis of maltol, J. Org. Chem. 39: 3281–3282, 1974.

Coleman, D. L., Lessons from studies with genetic forms of diabetes in the mouse. Metabolism 32: 162–164, 1983.

Davoren, P. R., The isolation of insulin from a single cat pancreas. Biochem. Biophys. Acta. 63: 150–153, 1962.

Drell, D. W., et al., Multiple immunological abnormalities in patients with type I (insulin-dependent) diabetes mellitus. Diabetologia 30: 132–143, 1987.

Dyrberg, T., et al., Humoral Immunity in the Spontaneously Diabetic BB Rat. Metabolism 32: 87–91, 1983.

Einsenbarth, G. Type I diabetes mellitus: a chronic autoimmune disease. N. Eng. J. Med. 314: 1360–1368, 1986.

Eun, H. M., et al., Role of cyclosporin A in macromolecular synthesis of pancreatic beta cells. Diabetes 36: 952–958, 1987.

(List continued on next page.)

Primary Examiner—T. J. Criares
Attorney, Agent, or Firm—Burns, Doane, Swecker & Mathis; T. Gene Dillahunty; Mary Ann Dillahunty

[57] ABSTRACT

This invention provides a method for preventing and/or treating diabetes in a mammal in need thereof comprising administering to the mammal an effective amount of at least one compound of the formula I:

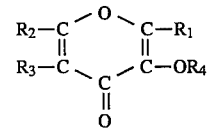

The invention also provides methods for preventing and/or treating diabetes comprising administering an effective amount of at least one compound of the formula I previously set forth and Orthosiphon Arestatus.

9 Claims, 3 Drawing Sheets

OTHER PUBLICATIONS

Farrar, G., et al., Tissue distribution of gallium following administration of the gallium–maltol complex in the rat: A model for an aluminum–maltol complex of neurotoxicological interest. Fd. Chem. Toxic 26: 523–525, 1988.

Finnegan, M. M., et al., Neutral water–soluble post–transition–metal chelate complexes of medical interest: Aluminum and gallium tris (3–hydroxy–4–pyronates), Inorg. Chem. 26: 2171–2176, 1987.

Gepts, W., Islet morphology in type I diabetes. Behring Inst. Mitt. 75: 39–41, 1984.

Gorsuch, A. N., et al., Evidence for a long prediabetic period in type I (insulin–dependent) diabetes. Lancet, 1363–1365, 1981.

Greene D. A., Metabolic Abnormalities in Diabetic Peripheral Nerve: Relation to Impaired Function. Metabolism 32: 118–123, 1983.

Hales, C. N., et al., Immunoassay of insulin with antibody precipitate. Biochem. J. 88: 137–142, 1963.

Hamet P., et al., Platelets and Vascular Smooth Muscle: Abnormalities of Phosphodiesterase, Aggregation, and Cell Growth in Experimental and Human Diabetes. Metabolism 32: 124–130, 1983.

Han, B. H., et al., Studies of the antioxidant components of Korean Ginseng. Proceedings of the 2nd International Ginseng Symposium, 13–17, 1978.

Han, B. H., et al., Chemical and Biological studies on sedative principle of zizyphus plant. Advances in New Drug Development, 381–390, 1991.

Haskins, K., et al., Acceleration of diabetes in young NOD mice with a CD4+ islet–specific T–cell clone. Science 249: 1433–1436, 1990.

Huber, S. Cytolytic T cells with demonstrated in the spleens of encephalomyocarditis virus infected DBA/2 mice which are lytic to beta cells in vitro. Metabolism 32: Abstracts 166, 1983.

Ihm, S. H., et al., Studies on autoimmunity for the initiation of beta cell destruction. VII. Evidence for antigenic changes on the beta cells leading to the autoimmune destruction of beta cells in BB rats. Diabetes 40: 269–274, 1991.

Ihm, S. H., et al., Studies on autoimmune mechanism for initiation of beta cell destruction: VI. Macropahges essential for development of beta cell–specific cytotoxic effectors and insulitis in NOD mice. Diabetes 39: 1273–1278, 1990.

Ihm, S. H., et al., Predisposing effect of anti–beta cell autoimmune process in NOD mice on the induction of diabetes by environmental insulitis. Diabetologic 33: 709–712, 1990.

Jackson, R., et al., Lymphocyte Abnormalities in the BB Rat. Metabolism 32: 83–86, 1983.

Katoka S., et al., Immunological aspects of the nonobese diabetic (NOD) mouse; abnormalities of cellular immunity. Diabetes 32; 247–253, 1983.

Kelsey, S. M., et al., Absorption of low and therapeutic doses of ferric maltol, a novel ferric iron compound, in iron deficient subjects using a single dose iron absorption test. J. of Clin. Phar. and Therapeutics 16: 117–122, 1991.

Ko, I. Y., et al., Studies on autoimmunity for the initiation of beta cell destruction. VIII. Pancreatic beta cell–dependent autoantibody to a 38 kD protein precedes the clinical onset of diabetes in BB rats. Diabetologia 34: 548–554, 1991.

Koevary, S., et al., Passive transfer of diabetes from BB/W to Wistar–Furth rats. J. Clin. Invest. 75: 1904–1907, 1985.

Koevary, S., et al., Passive transfer of diabetes in the BB/W rat. Science 220: 727–728, 1983.

Kontoghiorghes, G., Chelators affecting iron absorption in mice. Arzneim–Forsch./Drug Res. 40: 1332–1335, 1990.

Laupacis, A., et al., Cyclosporin prevents diabetes in BB Wistar rats. Lancet 1: 10–12, 1983.

Lee, K. U., et al., Evidence for initial involvement of macrophage in development of insulitis in NOD mice. Diabetes 37: 989–991, 1988.

Lee, K. U., et al., Preferential infiltration of macrophages during early stages of insulitis in diabetes–prone BB rats. Diabetes 37: 1053–1058, 1988.

Lee, K. U., et al., Prevention of lymphocytic thyroiditis and insulitis in diabetes–prone BB rats by the depletion of macrophages. Diabetologia 31: 400–402, 1988.

Like, A. A., et al., Prevention of diabetes in Biobreeding/Worcester rats with monoclonal antibodies that recognize T–lymphocytes or natural killer cells, J. Exp. Med. 164: 1145–1159, 1986.

Like, A. A., et al., Spontaneous diabetes mellitus in the BB/W rat: Effects of glucocorticoids, cyclosporin–A and antiserum to rate lymphocytes. Diabetes 32: 326–330, 1983.

Like, A. A., et al., Neonatal thymectomy prevents spontaneous diabetes mellitus in the BB/W rat. Science 216: 644–646, 1982.

Like, A. A., et al., Spontaneous diabetes mellitus: Reversal and prevention in the BB/W rat with antiserum to rat lymphocytes. Science 206: 1421–1423, 1979.

Maclaren N. K., et al., Autoimme Diatheses and T Lymphocyte Immunoincompetences in BB Rats. Metabolism 32: 92–96, 1983.

Madsen, O. D., Monoclonal antibodies against rat islet cells. Metabolism 32: Abstracts 165, 1983.

Marliss, E. B., et al., (Ed) The Juvenile Diabetes Foundation workshop on spontaneously diabetic BB rats as potential for insight into human juvenile diabetes. Metab. Clin. Exp. 32 (Suppl. 1) 1–66, 1983.

Marliss, E. B., et al., The diabetic syndrome of the "BB" Wistar rat: possible relevance to type I (insulin–dependent) diabetes in man. Diabetologia 22: 225–232, 1982.

McNeill, J. H., et al., Bis (maltolato) oxovanaduim (IV) is a potent insulin mimic, J. Med. Chem. 35:1489–1491, 1992.

Murray, F. T., et al., Gonadal Dysfunction in the Spontaneously Diabetic BB Rat. Metabolism 32: 141–147, 1983.

Nagata, M., et al., Studies on autoimmunity for T–cell–mediated beta cell destruction: Distinct difference in the destruction of beta cells between CD4+ and CD8+ T–cell clones derived from lymphocytes infiltrating the islets of NOD mice. Diabetes 41: 998–1008, 1992.

Onodera, T., et al., Virus–induced diabetes mellitus. Reovirus infection of pancreatic beta cells in mice. Science 201: 529–531, 1978.

Patel, S. T., Serum lipids and distribution pattern of lipoproteins of the BB wistar rat lipoproteins. Metabolism 32: Abstracts 166, 1983.

Peavy, D. E., Alterations in heptatic protein synthesis in spontaneously diabetic rats. Metabolism 32: Abstracts 165, 1983.

Raabo, E., et al., On the enzymatic determination of blood glucose. Scand. J. Clin. Lab. Invest. 12: 402–407, 1960.

Rajotte, R. V., et al., Low–Temperature Cryopreservation of BB Rat Embryos of Spontaneously Diabetic Rats. Metabolism 32: 156–161, 1983.

Reich, E. P., et al., An explanation for the protective effect of the MHC class II I–E molecule in murine diabetes. Nature 341: 326–329, 1989.

Reich, E. P., et al., Prevention of diabetes in NOD mice by injection of autoreactive T–lymphocytes. Diabetes 38: 1647–1651, 1989.

Rocic, B., et al., An investigation of the effect of vicinal polycarbonyl compounds on the β–Cells of the islets of langerhans of mice and rats. Diab. Croat. 14-3: 137–142, 1985.

Rossini, A. A., et al., Immunology of insulin–dependent diabetes mellitus. Ann. Rev. Immunol. 3: 289–320, 1985.

Rossini, A. A., et al. Failure to Transfer Insulitis to Athymic Recipients Using BB/W Rat Lymphoid Tissue Transplants. Metabolism, 32: 80–82, 1983.

Scott, F. W., Serum enzymes in the BB rat: Increased alkaline phosphatase in diatebtics. Metabolism 32: Abstracts 166, 1983.

Seemayer, T. A., et al., Lymphoproliferative Lesions in BB Wistar Rats. Metabolism 32: 97–100, 1983.

Sima, A. A. F., The Development and Structural Characterization of the Neuropathies in the Spontaneously Diabetic BB Wistar Rat. Metabolism 32: 106–111, 1983.

Sima, A. A. F., et al., The BB Wistar Rat: An Experimental Model for the Study of Diabetic Retinopathy. Metabolism 32: 136–140, 1983.

Srnka, C. A., Glomerular basement membrane in the spontaneously diabetic and nondiabetic wistar BB rat: In vivo and invitro studies of collagen synthesis and nonenzymatic glycosylation. Metabolism 32: Abstracts 165, 1983.

Suenaga, K., et al., Association of beta cell specific expression of endogenous retrovirus with the development of insulitis and diabetes in NOD mouse. Diabetes 37: 1722–1726, 1988.

Weeks, P. D., et al., Conversion of secondary furfuryl alcohols and isomaltol into maltol and related y–pyrones. J. Org. Chem. 45: 1109–1113, 1980.

Wright, J. R., Jr., et al., Pathological Lesions in the Spontaneously Diabetic BB Wistar Rat: A Comprehensive Autopsy Study. Metabolism 32:101–105. 1981.

Yoon, J. W., Viral pathogenesis of insulin–dependent diabetes mellitus: In: Autoimmunity and the pathogenesis of diabetes (Eds. F. Ginsberg–Felliner and R. C. McEvoy) Springer–Verlag, New York, 206–255, 1990.

Yoon, J. W., et al., Cultivation and characterization of murine pancreatic beta cells in a microculture system. In: Methods in Diabetes, edited by J. Larner and S. L. Pohl. John Wiley and Sons, Inc., I–B: 173–184, 1984.

Yoon, J. W., et al., Double labeled immunoflourescent techniques for the screening of diabetogenic viruses. In: Methods in Diabetes, edited by J. Larner and S. L. Pohl. John Wiley and Sons, Inc., I–A:313–326, 1984.

Yoon, J. W., et al., Virus–induced diabetes mellitus: Mengovirus infects pancreatic beta cells in strains of mice resistant to encephalomyocarditis virus. J. Virology 50: 684–690, 1984.

Yoon, J. W., et al., The initial step in the development of organ specific autoimmune disease in BB rats. Diabetologia 31: 779–780, 1988.

Yoon, J. W., et al., Virus–induced diabetes mellitus. XVIII. Inhibition by a non–diabetogenic variant of encephalomyocarditis virus. J. Exp. Med. 152: 878–892, 1980.

Yoon, J. W., et al., Virus–induced diabetes mellitus. XI. Replication of Coxsackie B3 virus in human pancreatic beta cell cultures. Diabetes 27: 778–781, 1978.

Yoon J. W. et al., Genetic differences in susceptibility of pancreatic B–cells to virus–induced diabetes mellitus. Nature 264:178–180, 1976.

Yoon, J. W., et al., Virus–induced diabetes mellitus. VI. Genetically determined host differences in the replication of encephalomyocarditis virus in pancreatic beta cells. J. Exp. Med. 143: 1170–1185, 1976.

Okamura, K., Maltol as a masking agent. Chem. Abs. 97: 108781x (1982).

Yoon, T., Maltol derivatives as antitumor agents. Chem. Abs. 117: 14433q (1992).

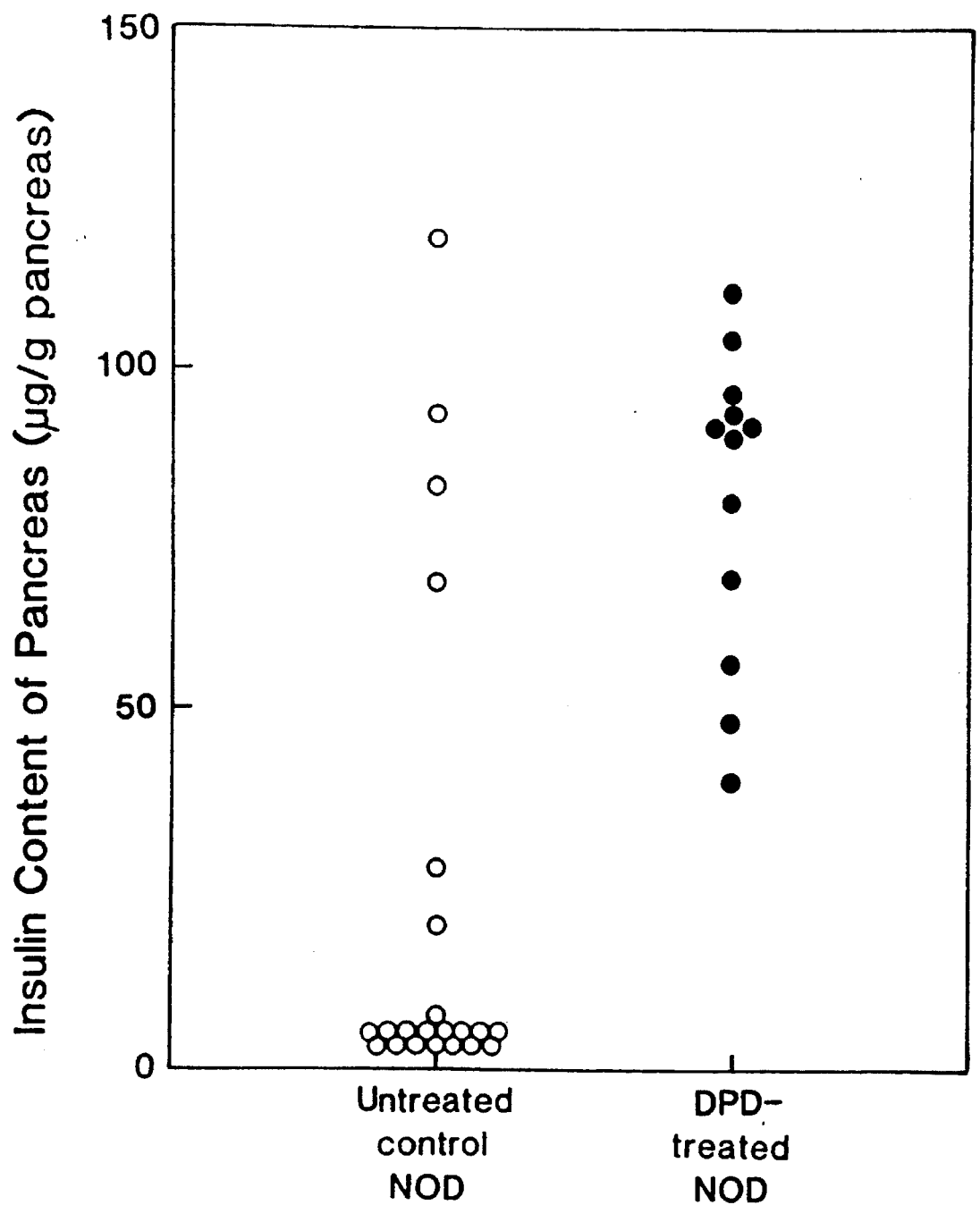

DIABETES PREVENTION AND TREATMENT USING GAMMA-PYRONES

CROSS-REFERENCE TO RELATED APPLICATIONS

This application is a continuation-in-part of U.S. application Ser. No. 07/978,958 filed Nov. 23, 1992, now U.S. Pat. No. 5,298,525 which is incorporated herein by reference.

FIELD OF THE INVENTION

This invention relates to prevention and treatment of diabetes.

REFERENCES The following references are cited in the application as superscript numbers at the relevant portion of the application.

1. Gorsuch, A. N., Spencer, K. N., Lister, J., McNally, J. M., Dean, B. M., Bottazzo, G. F., Cudworth, A. G. Evidence for a long prediabetic period in type I (insulin-dependent) diabetes. Lancet 2: 1363–1365, 1981.
2. Yoon, J. W. Viral pathogenesis of insulin-dependent diabetes mellitus: In: Autoimmunity and the pathogenesis of diabetes (Eds. F. Ginsberg-Felliner and R. C. McEvoy) Springer-Verlag, New York, pp. 206–255, 1990.
3. Rossini, A. A., Mordes, J. P., Like, A. A. Immunology of insulin-dependent diabetes mellitus. Ann. Rev. Immunol. 3:289–320, 1985.
4. Drell, D. W., Notkins, A. L. Multiple immunological abnormalities in patients with type I (insulin-dependent) diabetes mellitus. Diabetologia 30: 132–143, 1987.
5. Gepts, W. Islet morphology in type I diabetes. Behring Inst. Mitt. 75: 33–38, 1984.
6. Einsenbarth, G. Insulin dependent diabetes mellitus: a chronic autoimmune disease. N. Eng. J. Med. 314: 1360–1368, 1986. 7. Cahill, G.F., McDevitt, H. O. Insulin-dependent diabetes mellitus: the initial lesion, N. Eng. J. Med. 304: 1454–1455, 1981. 8. Katoka, S., Satoh, J., Fujiya, H., Toyota, T., Suzuki R., Itoh, K., Kumagai, K. Immunological aspects of the nonobese diabetic (NOD) mouse; abnormalities of cellular immunity. Diabetes 32: 247–253, 1983.
9. Lee, K. U., Amano, K. and Yoon, J. W. Evidence for the initial involvement of macrophage in the development of insulitis in non-obese diabetic (NOD) mice. Diabetes 37: 989–991, 1988.
10. Suenaga, K. and Yoon, J. W. Association of beta cell specific expression of endogenous retrovirus with the development of insulitis and diabetes in NOD mouse. Diabetes 37: 1722–1726, 1988.
11. Ihm, S. H. and Yoon, J. W. Autoimmune mechanism for the initiation of beta cell destruction: VI. Macrophages are essential for the development of beta cell-specific cytotoxic effector immunocytes and insulitis in nonobese diabetic (NOD) mice. Diabetes 39: 1273–1278, 1990.
12. Ihm, S. H., Lee, K. U., McArthur, R. G. and Yoon, J. W. Predisposing effect of anti-beta cell autoimmune process in NOD mice on the induction of diabetes by environmental insulitis. Diabetologia 33: 709–712, 1990.
13. Marliss, E. B., (Ed) The Juvenile Diabetes Foundation workshop on spontaneously diabetic BB rats as potential for insight into human juvenile diabetes. Metab. Clin. Exp. 32 (Suppl 1) 1–66, 1983.
14. Marliss, E.B., Nakhooda, A. F., Poussier, P., Simma, A. A. F. The diabetic syndrome of the "BB" Wistar rat: possible relevance to type I (insulin-dependent) diabetes in man. Diabetologia 22: 225–232, 1982.
15. Like, A. A., Kislauskis, E., Williams, R. M., Rossini, A.A. Neonatal thymectomy prevents spontaneous diabetes mellitus in the BB/W rat. Science 216: 644–646, 1982.
16. Like, A. A. Anthony, M., Guberski, D. L., Rossini, A. A. Spontaneous diabetes in the BB/W rat: Effects of glucocorticoids, cyclosporin-A and antiserum to rat lymphocytes. Diabetes 32: 326–330, 1983.
17. Like, A. A. Rossini, A. A. Appel. M. C., Guerski, D. L., Williams, R. M. Spontaneous diabetes mellitus: reversal and prevention in the BB/W rat with antiserum to rat lymphocytes. Science 206: 1421–1423, 1979.
18. Laupacis, A., Stiller, C. R., Cardell, C., Keown, P., Dupre, J., Wallace, A. C., Thibert, P. Cyclosporin prevents diabetes in BB Wistar rats. Lancet 1:10–12, 1983.
19. Like, A. A., Biron, C. A., Weringer, E. J., Byman, K., Sroczynski, E., Guberski, D. L. Prevention of diabetes in Biobreeding/Wistar rats with monoclonal antibodies that recognize T-lymphocytes or natural killer cells, J. Exp. Med. 164: 1145–1159, 1986.
20. Koevary, S., Rossini, A. A., Stoller, W., Chick, W. Passive transfer of diabetes in the BB/W rat. Science 220: 727–728, 1983.
21. Koevary, S., Williams, D. E., Williams, R. M., Chick, W. Passive transfer of diabetes from BB/W to Wistar-Furth rats. J. Clin. Invest. 75: 1904–1907, 1985.
22. Lee, K. U., Kim, M. K., Amano, K., Pak, C. Y., Jaworski, M. A., Metha, J. G. and Yoon, J. W. Preferential infiltration of macrophages in the early stages of insulitis precedes the involvement of activated T-lymphocytes in the spontaneously diabetic BB rat. Diabetes 37: 1053–1058, 1988.
23. Lee, K. U., Pak, C. Y., Amano, K and Yoon, J. W. Prevention of lymphocytic thyroiditis and insulitis in diabetes-prone BB rats by the depletion of macrophages. Diabetologia 31: 400–402, 1988.
24. Amano, K. and Yoon, J. W. Autoimmune mechanisms for the initiation of beta cell destruction: V. Prevention of diabetes in silica-treated BB rats is due to a decrease in macrophage-dependent T-effector cells and natural killer cytotoxicity. Diabetes 39: 590–596, 1990.
25. Ko, I. Y., Ihm, S. H. and Yoon, J. W. Studies on autoimmunity for the initiation of beta cell destruction. VIII. Pancreatic beta cell-dependent autoantibody to a 38 Kd protein precedes the clinical onset of diabetes in BB rats. Diabetologia 34: 548–554, 1991.
26. Ihm, S. H., Lee, K. U. and Yoon, J. W. Studies on autoimmunity for the initiation of beta cell destruction. VII. Evidence for antigenic changes on the beta cells leading to the autoimmune destruction of beta cells in BB rats. Diabetes 40: 269–274, 1991.
27. Nagata, M. and Yoon, J. W. Studies on autoimmunity for T-cell-mediated beta cell destruction: Distinct dif- 27. ference in the destruction of beta cells between CD4+ and CD8+ T-cell clones derived from lymphocytes infiltrating the islets of NOD mice. Diabetes 41: 998–1008, 1992.

28. Bach, J. F. Mechanisms of autoimmunity in insulin-dependent diabetes mellitus. Clin. Exp. Immunol. 72: 1–8, 1988.

29. Brennan, T. M., Weeks, P. D., Brannegan, D. P., Kuhla, D. E., Elliott, M. L., Watson, H. A. and Wlodecki, B. A novel synthesis of maltol and related γ-pyrones. Tetrahedron Letters, 331–333, 1978.

30. Chawla, R. K. and McGonigal, W. E., A new synthesis of maltol, J. Org. Chem. 39:3281–3282, 1974.

31. Weeks, P. D., Brennan, T. M. Brannegan, D. P., Kuhla, D. E., Elliott, M. L., Watson, H. A., Wlodecki, B. and Breitenbach, R. Conversion of secondary furfuryl alcohols and isomaltol into maltol and related γ-pyrones. J. Org. Chem. 45:1109–1113, 1988.

32. Han, B. M., Park, M. H., Woo, L. K., Woo, W. S. and Han, Y. N.: Studies of the antioxidant components of Korean Ginseng. Proceedings of the 2nd International Ginseng Symposium, 13–17, 1978.

33. Davoren, P.R. The isolation of insulin from a single cat pancreas. Biochem. Biophys. Acta. 63: 150–153, 1962.

34. Yoon, J.W. and Notkins, A.L., Virus-induced diabetes mellitus. VI. Genetically determined host differences in the replication of encephalomyocarditis virus in pancreatic B-cells. J. Exp. Med. 143: 1170–1185, 1976.

35. Asayama, K., English, D., Slonim, A. E. and Burr, I. M. Chemiluminescence as an index of drug-induced free radical production in pancreatic islets. Diabetes 33: 160–163, 1984.

36. Asayama, K., Nyfeler, F., English, D., Pilkis, S. J. and Burr, I. M. Alloxan-induced free-radical production in isolated cells: Selective effect on islet cells. Diabetes 33: 1008–1011, 1984.

37. Yoon, J. W., Bachurski, C. J., Shin, S. Y., and Archer, J. Isolation, cultivation and characterization of murine pancreatic beta cells in microculture system. In: Methods in Diabetes, edited by S. L. Pohl and J. Larner. John Wiley and Sons, Inc., Vol. 1-B: 173–184, 1984.

38. Lee, K. U., Amano, K. and Yoon, J. W. Evidence for the initial involvement of macrophage in the development of insulitis in non-obese diabetic (NOD) mice. Diabetes 37: 989–991, 1988.

39. Raabo, E. Terkildsen, T. C. On the enzymatic determination of blood glucose. Scand. J. Clin. Lab. Invest. 12: 402–407, 1960.

40. Yoon, J. W. McClintock, P. R. Onodera, T. and Notkins, A. L. Virus-induced diabetes mellitus. Inhibition by a non-diabetogenic variant of encephalomyocarditis virus. J. Exp. Med. 152: 878–892, 1980.

41. Yoon J. W., Lesniak, M. A., Fussganger, R. and Notkins, A. L. Genetic differences in susceptibility of pancreatic B-cells to virus-induced diabetes mellitus. Nature 264: 178–180, 1976.

42. Hales, C. N. and Randle, P. J. Immunoassay of insulin with antibody precipitate. Biochem. J. 88: 137–142, 1963.

43. Onodera, T., Jenson, A. B., Yoon, J. W. and Notkins, A. L. Virus-induced diabetes mellitus. Reovirus infection of pancreatic beta cells in mice. Science 301: 529–531, 1978.

44. Yoon, J. W., Morishima, T., McClintock, P. R., Austin, M., and Notkins, A. L. Virus-induced diabetes mellitus: Mengovirus infects pancreatic beta cells in strains of mice resistant to encephalomyocarditis virus. J. Virology 50: 684–690, 1984.

45. Yoon, J. W. and Bachurski, C. J. Double labeled immunofluorescent techniques for the screening of diabetogenic viruses. In: Methods in Diabetes, edited by S. L. Pohl and J. Larner. John Wiley and Sons, Inc., Vol. 1-A: 313–326, 1984.

46. Yoon, J. W., Onodera, T., Jenson, A. B. and Notkins, A. L. Virus-induced diabetes mellitus. XV. Replication of Coxsackie B3 virus in human pancreatic beta cell cultures. Diabetes 27: 778–781, 1978.

47. Eun, H. M., Pak, C. Y., Kim, C. J., McArthur, R. G. and Yoon, J. W.: Role of cyclosporin A in macromolecular synthesis of pancreatic beta cells. Diabetes 36: 952–958, 1987.

48. Baek, H. S. and Yoon, J. W. Direct involvement of macrophages in destruction of β-cells leading to development of diabetes in virus-infected mice. Diabetes 40: 1586–1597, 1991.

49. Baek, H. S. and Yoon, J. W. Role of macrophages in the pathogenesis of encephalomyocarditis virus-induced diabetes in mice. J. Virology 64: 5708–5715, 1990.

50. Reich, E. P., Sherwin, R. S., Kanagawa, O., Janeway, C. A. Jr. An explanation for the protective effect of the MHC class II I-E molecule in murine diabetes. Nature 341: 326–329, 1989.

51. Haskins, K., McDuffie, M. Acceleration of diabetes in young NOD mice with a CD4+ islet-specific T-cell clone. Science 249: 1433–1436, 1990.

52. Nagata, M. and Yoon, J. W. Studies on autoimmunity for T-cell-mediated beta cell destruction: Distinct difference in beta cell destruction between CD4+ and CD8+ T-cell clones derived from lymphocytes infiltrating the islets of NOD mice. Diabetes 41: 998–1008, 1992.

53. Reich, E. P., Scaringe, D., Yagi, J., Sherwin, R. S., Janeway, C. A. Jr. Prevention of diabetes in NOD mice by injection of autoreactive T-lymphocytes. Diabetes 38: 1647–1651, 1989.

54. Hider, R. C. et al. Pharmaceutical compositions, U.S. Pat. No. 4,575,502, 1986.

55. Hider, R. C. et al. Pharmaceutical compositions and methods for increasing zinc levels, U.S. Pat. No. 4,665,064, 1987.

56. Shah, M. Orally administrable gallium compositions and methods of treatment therewith, PCT Application No. PCT/US91/03599, 1991.

57. Silver, J. Pharmaceutical compositions, PCT Application No. PCT/GB87/00400, 1987.

58. McNeill, J. H. et al. Bis (maltolato) oxovanadium (IV) is a potent insulin mimic, J. Med. Chem. 35:1489–1491, 1992.

59. Ward, W. K., Beard, J. C., Halter, J. B., Pfeifer, M. A. and Porter, D. Pathophysiology of insulin secretion in non-insulin-dependent diabetes mellitus. Diabetes Care 7:491–502, 1984.

60. Lang, D. A., Matthews, D. R., Burnett, M. and Turner, R. C. Brief, irregular oscillations of basal plasma insulin and glucose concentrations in diabetic man. Diabetes 30:435–439.3, 1981.

61. Goto, Y., Kakizaki, M., and Masaki, N. Spontaneous diabetes produced by selective breeding of hormal wistar rats. Proc. Jpn. Acad. 51:80–85, 1975.

62. Sugiyama, Y., Odake, H., Shimura, Y., Ikeda, H., Matsuo, T., Abe, S., Suzuki, K., and Goto, Y. Role of hepatic insulin sensitivity in development of hyperglycemia of spontaneously diabetic GK Rats. J. Japan Diab. Soc. 32:593–599, 1989.

63. Suzuki, S., Taneda, Y., Hirai, S., Abe, S., Saski, A., Suzuki, K-I, and Toyota, T. Molecular mechanisms of insulin resistance in spontaneous diabetic GK (Goto-Kaizaki) rats. In: New Directions in research and clinical works for obesity and diabetes mellitus. Elsevier Science Publishers B.V., pp. 197–203, 1991.

64. Yoon, J. W., McClintock, P. R., Onodera, T. and Notkins, A. L. Virus-induced diabetes mellitus. Inhibition by a non-diabetogenic variant of encephalomyocarditis virus. J. Exp. Med. 152:878–892, 1980.

65. Yoon, J. W., Onodera, T. and Notkins, A. L. Virus-induced diabetes mellitus: Beta cell damage and insulin-dependent hyperglycemia in mice infected with Coxsackie virus B4. J. Exp. Med. 148:1068–1080, 1978.

66. Toniolo, A., Onodera, T., Yoon, J. W. and Notkins, A. L. Induction of diabetes by cumulative environmental insults from viruses and chemicals. Nature 288:383–385, 1980.

67. Yoon, J. W., Morishima, T., McClintock, P. R., Austin, M., and Notkins, A. L. Virus-induced diabetes mellitus: Mengovirus infects pancreatic beta cells in strains of mice resistant to encephalomyocarditis virus. J. Virol. 50:684–690, 1984.

The disclosure of the above publications, patents and patent applications are herein incorporated by reference in their entirety to the same extent as if the language of each individual publication, patent and patent application were specifically and individually included herein.

BACKGROUND OF THE INVENTION

Diabetes mellitus and its complications are now considered to be the third leading cause of death in Canada and the United States, trailing only cancer and cardiovascular disease. According to a report issued by the National Commission on Diabetes, as many as 10 million North Americans may have diabetes, and the incidence is increasing yearly. Although the acute and often lethal symptoms of diabetes can be controlled by insulin therapy, the long-term complications reduce life expectancy by as much as one third. Compared with rates of incidence in nondiabetic normal persons, diabetic patients show rates which are increased 25-fold for blindness, 17-fold for kidney disease, 5-fold for gangrene, and 2-fold for heart disease.

There are 2 major forms of diabetes mellitus. One is type I diabetes, which is also known as insulin-dependent diabetes mellitus (IDDM), and the other is type II diabetes, which is also known as noninsulin-dependent diabetes mellitus (NIDDM). Most patients with IDDM have a common pathological picture: the nearly total disappearance of insulin-producing pancreatic beta cells which results in hyperglycemia[1-7].

Considerable evidence has been accumulated showing that most IDDM is the consequence of progressive beta-cell destruction during an asymptomatic period often extending over many years[1-7]. The prediabetic period can be recognized by the detection of circulating islet-cell autoantibodies and insulin autoantibodies. The hypothesis that IDDM is an autoimmune disease has been considerably strengthened by studies on the nonobese diabetic (NOD) mouse[8-12] and the BioBreeding (BB) rat[13-27]. Both of these animals develop IDDM spontaneously and their diabetic syndromes share many pathological features with that of humans with IDDM.

Type II diabetes, also known as non-insulin-dependent diabetes mellitus (NIDDM), is much more common than IDDM, affecting 90% of all persons with diabetes. NIDDM is a mild form of diabetes, often of gradual onset, which usually appears in middle age (over 40 years of age). The pathological changes in the pancreatic islets in patients with NIDDM are not always apparent. Moreover, the clinical manifestations of NIDDM are frequently mild, and high glucose levels in the blood can usually be controlled by diet alone. Although diabetes is traditionally viewed as a condition caused by a deficiency of insulin, many patients with NIDDM have normal to high plasma insulin levels. In these individuals, diabetes arises not from a shortage of insulin, but probably from a defect in the molecular machinery that medicates the action of insulin on its target cells.

A number of hypotheses have been put forward to explain NIDDM, including insulin resistance, down regulation of insulin receptors, and problems with the glucose transport system. In NIDDM, insulin resistance results in a reduction in the biological response to insulin of about 40%. Insulin lowers blood glucose through two separate mechanisms, namely, by suppressing glucose release from the liver, and by promoting uptake of glucose in the peripheral tissues, particularly muscle. In NIDDM, the responsiveness of peripheral tissues to insulin is substantially impaired[59]. There are also some data suggesting that hepatic glucose output is less easily suppressed by insulin in NIDDM, implying that the liver shares in the insulin resistance[60]. Hyperglycemia itself can also cause insulin resistance and impaired insulin secretion, but many factors also contribute to the insensitivity including obesity, age, lack of exercise, diet and genetic components. The mechanisms of insulin resistance in NIDDM are unclear but may involve reduced insulin receptor numbers (secondary to hyperinsulinaemia and hyperglycemia), reduced tyrosine kinase of the insulin receptors, and abnormalities distal to the receptors.

The major intracellular actions of insulin are stimulation of both nutrient uptake and biosynthetic processes. Glucose uptake is enhanced by increasing glucose transporters on the cell surface, probably by promoting their translocation from intracellular pools. NIDDM may occur because of a decreased number of glucose transporters on the target cell surface. If this is so, NIDDM is not caused by beta cell destruction, but by other mechanisms.

The GK rat is considered to be one of the best animal models for NIDDM, and is characterized by impaired glucose-insulin secretion and peripheral insulin resistance[61,62]. Insulin response and sensitivity of glycogen synthesis, lipogenesis and DNA synthesis in hepatocytes from GK rats are markedly reduced as compared to non-diabetic control rats such as Wistar-Furth (WF). Insulin binding activity in adipocytes and hepatocytes from the GK rat are not different from those of control rats, suggesting that insulin resistance might result from a post-binding defect. Insulin-induced generation of inositol glycan is also markedly reduced in adipocytes and hepatocytes from the GK rat as compared with non-diabetic control WF rats. Two inositol anomers, myo-inositol and chiro-inositol are essential components of inositol glycans. The urinary secretion of chiro-inositol in GK rats in much lower than in control rats. In contrast, the urinary secretion of myoinositol is higher in the GK rat than in control rats. On the basis of these results, Suzuki et al.[63] suggest that reduced generation of inositol glycan and altered metabolism of inositol anomers may contribute to the post-binding defect in insulin resistance in the GK rat.

Diabetes research has been directed toward prevention and cure of IDDM. To date, therapy of IDDM in humans by methods designed to suppress the autoimmune response has proved to be largely unsuccessful. Immunosuppressive therapy utilizing glucocorticoids and cyclophosphamide did not alter the course of the disease. Although studies on the use of cyclosporin A in diabetes appear to be encouraging, generalized immunosuppression involves potential complications including infections and drug-induced kidney and liver damage.

There is a need for a compound which would be nontoxic and have no side effects but which would prevent clinical IDDM and/or NIDDM completely. A preferred drug would be administered noninvasively, such as an orally administered solution or tablet.

SUMMARY OF THE INVENTION

One aspect of the invention provides a method for preventing type II diabetes in a mammal susceptible to developing said diabetes comprising administering to said mammal an effective amount of at least one compound of the formula I:

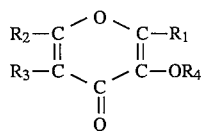

wherein $R_1$, $R_2$ and $R_3$ are independently selected from the group consisting of H, an alkyl of from 1 to 8 carbon atoms, an alkyl-o-alkyl of from 2 to 8 carbon atoms, a haloalkyl of from 1 to 8 carbon atoms and 1 to 3 halogen atoms, an alkenyl of from 2 to 8 carbon atoms with one site of unsaturation, ketones of from 2 to 8 carbon atoms, aldehydes of from 1 to 8 carbon atoms, and any of the above compounds which are alcohol-substituted; and $R_4$ is either H or $-COR_5$, wherein $R_5$ is an alkyl of from 1 to 5 carbon atoms; or a salt thereof.

Another aspect of the invention provides a method for the treatment of type I diabetes in a mammal exhibiting characteristics of said diabetes comprising administering to said mammal an effective amount of at least one compound of the formula I previously set forth.

A further aspect of the invention provides a method for preventing or treating any diabetes in a mammal comprising: a) administering to said mammal an effective amount of at least one compound of the formula I previously set forth; and b) administering to said mammal another modality useful for preventing or treating said diabetes.

BRIEF DESCRIPTION OF THE DRAWINGS

FIG. 3 illustrates that DPD treatment prevents depression of pancreatic insulin levels in NOD mice.

DETAILED DESCRIPTION OF THE INVENTION

A. Definitions

Figure 1:
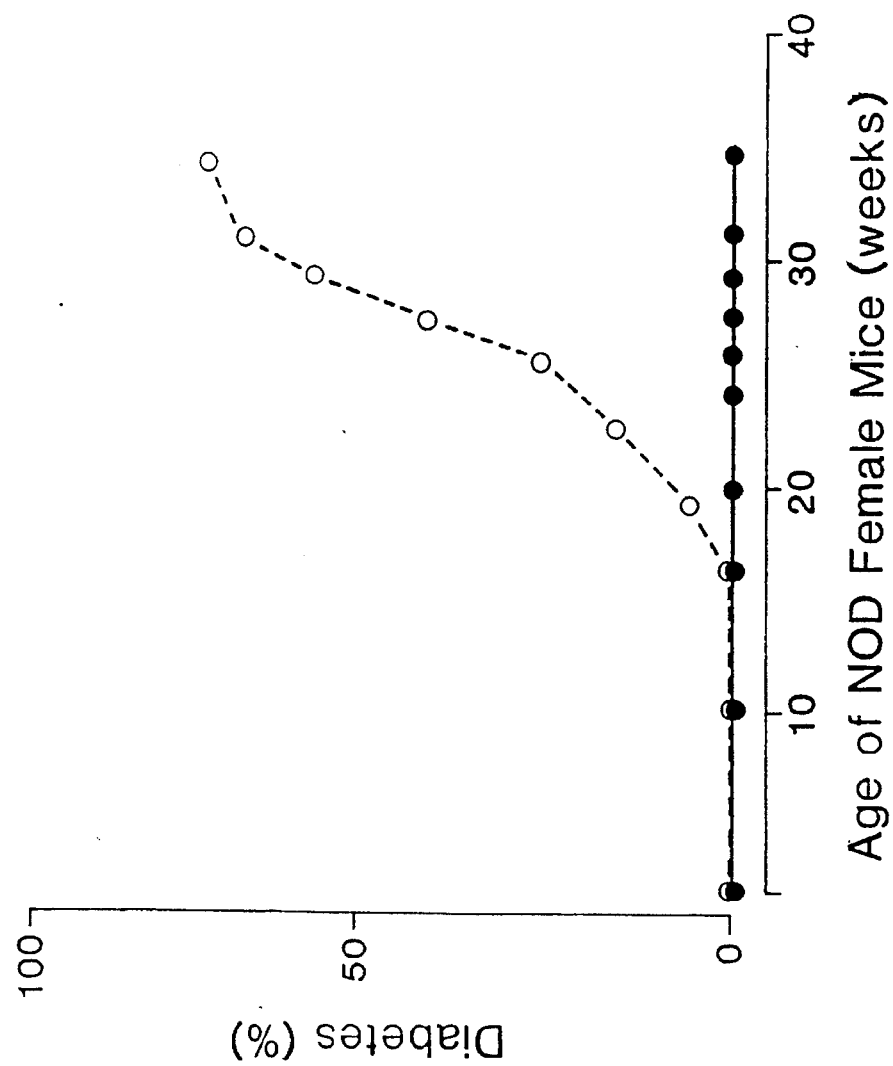
FIG. 1 illustrates that treatment with DPD prevents the onset of clinical diabetes in NOD mice as evidenced by urine glucose values.

As used herein the following terms have the following meanings:

DPD: diabetes prevention drug, γ-pyrones including maltol and maltol-related compounds with the formula I previously set forth.

OSA: Orthosiphon aristatus, also known as Clerodendron or Clerodendrathus spicatus, a plant recorded in Dutch pharmacopoeias. The plant is used to dissolve kidney stones, and has been traditionally used to clear up heat, remove dampness, promote diuresis, and excrete calculus. Thus, this plant has been applied to treatment of chronic nephritis, cystitis, urethral calculus, and arthritis. The chemical constituents of the plant include potassium sulfate, calcium salts, potassium salts, volatile oil, pentose, saponins, and hexose. The leaf of the plant contains myoinositol. Other species of orthosiphon, such as O. grandiflorus may contain potassium nitrate, bitter glycosides, orthosiphonin, ursolic acid and β-sitosterol.

Type I diabetes: severe diabetes mellitus, usually of abrupt onset prior to maturity, characterized by low plasma insulin levels, polydipsia, polyuria, increased appetite, weight loss and episodic ketoacidosis; also referred to as IDDM.

Type II diabetes: an often mild form of diabetes mellitus, often of gradual onset, usually in adults, characterized by normal to high absolute plasma insulin levels which are relatively low in relation to plasma glucose levels; also referred to as NIDDM.

B. Synthesis and Methodology

With regard to the preparation of γ-pyrones which are useful in the present invention, certain of these compounds occur naturally and may be obtained by extraction from natural sources. For example, maltol is found in ginseng the bark of the young larch tree, in pine needles, chicory, wood tars and oils, and roasted malt.

Certain of the γ-pyrones are available commercially, including maltol and ethyl maltol. Others can be made from pyromeconic acid as a starting material, which can be derived from meconic acid. Methods of preparing such compounds are well known in the art [29-31]. Additionally, it is noted that maltol and ethyl maltol are in widespread use as flavoring and fragrance-enhancing agents for foods, and have very low toxicities when taken orally.

Maltol and related γ-pyrones have also been used to complex with or as a chelator for metals such as vanadium, chromium, zinc, gallium or iron to increase the absorption of the metals by the body[54-58]. Such metal-maltol complexes may be useful in treating metal deficiencies.

It is expected that several γ-pyrones will be useful in the present invention. In particular, γ-pyrones of the formula I previously set forth or salts thereof are preferred. Maltol and ethyl maltol are especially preferred due to their low toxicity and suitability for oral administration.

C. Pharmaceutical Compositions

The methods of this invention are achieved by using a pharmaceutical composition comprising one or more effective γ-pyrone compounds (DPD).

When used for oral administration, which is preferred, DPD may be formulated in a variety of ways. It will preferably be in solid form, and may optionally and conveniently be used in compositions containing a pharmaceutically inert carrier, including conventional solid carriers such as lactose, starch, dextrin or magnesium stearate, which are conveniently presented in tablet or capsule form. DPD itself may also be used without the addition of inert pharmaceutical carriers, particularly for use in capsule form.

Compositions including a liquid pharmaceutically inert carrier such as water may also be considered for oral administration. Other pharmaceutically compatible liquids may also be used. The use of such liquids is well known to those of skill in the art.

Doses are selected to provide prevention of the development of diabetes or treatment of diabetes. Useful doses are expected to be from about 1 to 100 mg/kg/day, preferably about 20 to 30 mg/kg/day. Administration is expected to be daily. The dose level and schedule of administration may vary depending on the particular γ-pyrone(s) used and such factors as the age and condition of the subject.

Administration of DPD during the period from birth to maturity will be useful in preventing the onset of clinical diabetes in those predisposed to this disease. It is expected that treatment with DPD from one month to 10 years of age will be especially useful in preventing type I diabetes.

As discussed previously, oral administration is preferred, but formulations may also be considered for other means of administration such as per rectum, transdermally, and parenterally by intravenous, subcutaneous and intramuscular injection. The usefulness of these formulations may depend on the particular compound used and the particular subject receiving the DPD. These formulations may contain a liquid carrier that may be oily, aqueous, emulsified or contain certain solvents suitable to the mode of administration.

Compositions may be formulated in unit dose form, or in multiple or subunit doses. For the expected doses set forth previously, each tablet or capsule should preferably contain about 100 mg DPD. Orally administered liquid compositions should preferably contain about 20 mg DPD/mL.

When used in conjunction with other treatment modalities, the formulation will depend on the other treatment used. If the other treatment is administered by the same route as DPD, they may be formulated together as in any of the compositions described above. For example, in the case of combined treatment with OSA and DPD, both may be given orally in an aqueous solution containing appropriate amounts of each.

D. Use of DPD for Prevention and Treatment of Diabetes

The compositions and methods of this invention are useful in preventing and treating diabetes. To date, therapy of IDDM in humans by methods designed to suppress the autoimmune response has proven to be largely unsuccessful. Immunosuppressive therapy utilizing glucocorticoids and cyclophosphamide did not alter the course of the disease. Although studies on the treatment of diabetes with cyclosporin A appear to be encouraging, generalized immunosuppression involves potential complications including infections and drug-induced kidney and liver damage. In addition, long-term treatment is potentially carcinogenic in some cases. One aspect of the subject invention is drawn to the surprising discovery that oral administration of DPD, a non-toxic compound, prevents type I diabetes.

The target population in humans for DPD administration is any one with a family history of type I diabetes or any one who suffers from type II diabetes. This includes individuals with siblings who have type I diabetes. More genetically specific target populations may include individuals who are HLA DR3+and/or HLA DR4+, those who are HLA-, those who are ICA positive, and those with non-aspartic acid at the 57 amino acid position of the HLA-DQ$_\beta$chain and/or arginine at the 52 amino acid position of HLA-DQ$_\alpha$chain. The potential utility for such a drug is vast.

Several maltol-related compounds, of the formula I previously set forth or salts thereof, will also be useful in the compositions and methods of the present invention. Maltol and ethyl maltol are preferably used.

Maltol was 100% successful in preventing clinical diabetes in NOD mice. Several immunosuppressive candidate drugs have been suggested for the control of diabetes but none has proved to be successful in 100% of cases. Furthermore, many of the drugs already tested cannot be used on a long-term basis due to the potential for side effects and the development of complications. Maltol and ethyl maltol, as evidenced by their approval for use in foods, can be used for a lifetime with no side effects. In addition, it is common for diabetes to occur after cessation of treatment with previously tested drugs. In experiments with DPD-treated NOD mice, there was no recurrence of the disease during the testing period (35 weeks), which included 15 weeks of study after cessation of treatment.

In addition to the effect of the DPD on Type I diabetes (IDDM), compounds of the formula I previously set forth are also effective in treating Type II diabetes (NIDDM). Experimental results from work with the NOD mouse and GK rat provide evidence to support this.

Treatment of NOD mice with DPD not only substantially protects against beta cell destruction, but also appears to affect control of glucose metabolism. Experimental results from DPD-treated NOD mice (history of pancreatic islets, immunofluorescent staining of pancreatic islet cells, and insulin content of the pancreata) reveal that while there is beta cell destruction, these animals do not exhibit hyperglycemia. The level of beta cell destruction observed in DPD-treated NOD mice is also significantly lower than that observed in untreated diabetic NOD mice. Without being limited to any theory, the prevention of diabetes in DPD-treated animals may be due to the significantly lowered level of beta cell destruction, or to the combined effects of reduced beta cell destruction and control of blood glucose by DPD.

Type II diabetes is not caused by beta cell destruction, but by other mechanisms such as insulin resistance, down regulation of insulin receptors, and/or changes to the glucose transport system. Again, without being limited to any theory, it is contemplated that DPD would act on both protection of beta cell destruction and control of blood glucose metabolism, so that DPD would be effective in the treatment of Type II diabetes as it should increase insulin sensitivity, cause up regulation of insulin receptors and/or improve glucose metabolism.

Accordingly, it was expected that DPD would be effective in treating type II diabetes in animals exhibiting NIDDM. The method of treatment comprises administering an effective amount of at least one compound of the formula I set forth previously. Maltol and ethyl maltol are preferably used and administration is preferably oral.

The methods and compositions of the present invention may also be used in conjunction with other treatment modalities, including conventional treatment for type I and type II diabetes.

Studies of the effect of DPD on type II diabetes in GK rats showed that administration of DPD caused some reduction of blood glucose levels. When DPD was used in conjunction with other modalities, even greater reduction was seen. For example, treatment with DPD and OSA resulted in significantly reduced blood glucose levels (185 mg/dl for treated animals versus 392 mg/dl for controls).

It is expected that DPD will also be useful for inhibiting further development of type I diabetes in animals demonstrating incipient type I diabetes. Incipient type I diabetes may be demonstrated by using genetic markers. In particular, in humans, treatment of individuals who are HLA DR3+and/or HLA DR4+, those who are HLA-, those who are ICA positive, and those with non-aspartic acid at the 57 amino acid position of the HLA-DQ$_{62}$ chain and/or arginine at the 52 amino acid position of HLA-DQ$_{60}$ chain with DPD will prevent any further development of type I diabetes. The method of inhibition comprises administering an effective amount of at least one compound of the formula I set forth previously. Maltol and ethyl maltol are preferably used and administration is preferably oral.

E. Examples

The NOD mouse is one of the best animal models for autoimmune type I diabetes in humans [8]. NOD mice spontaneously develop type I diabetes and their syndrome shares many pathological features with type I diabetes in humans. The diabetic syndrome in NOD mice results from the destruction of pancreatic beta cells by cell-mediated and/or humoral immune responses [8-12]. Extensive experimental results provide clear evidence for involvement of cell-mediated immunity in the development of diabetes in NOD mice [8,28]. Recent experimental results indicate that macrophages [9,11] and T lymphocytes are involved in the pathogenesis of autoimmune type I diabetes in NOD mice [27]. NOD mice were dosed with DPD for 18 weeks, and this treatment with DPD prevented clinical diabetes completely. These results will be discussed in detail in the Examples that follow.

The following examples are offered to illustrate this invention and are not meant to be construed in any way as limiting the scope of this invention.

EXAMPLE 1

Prevention of Clinical Diabetes in NOD Mice using DPD

Figure 2:
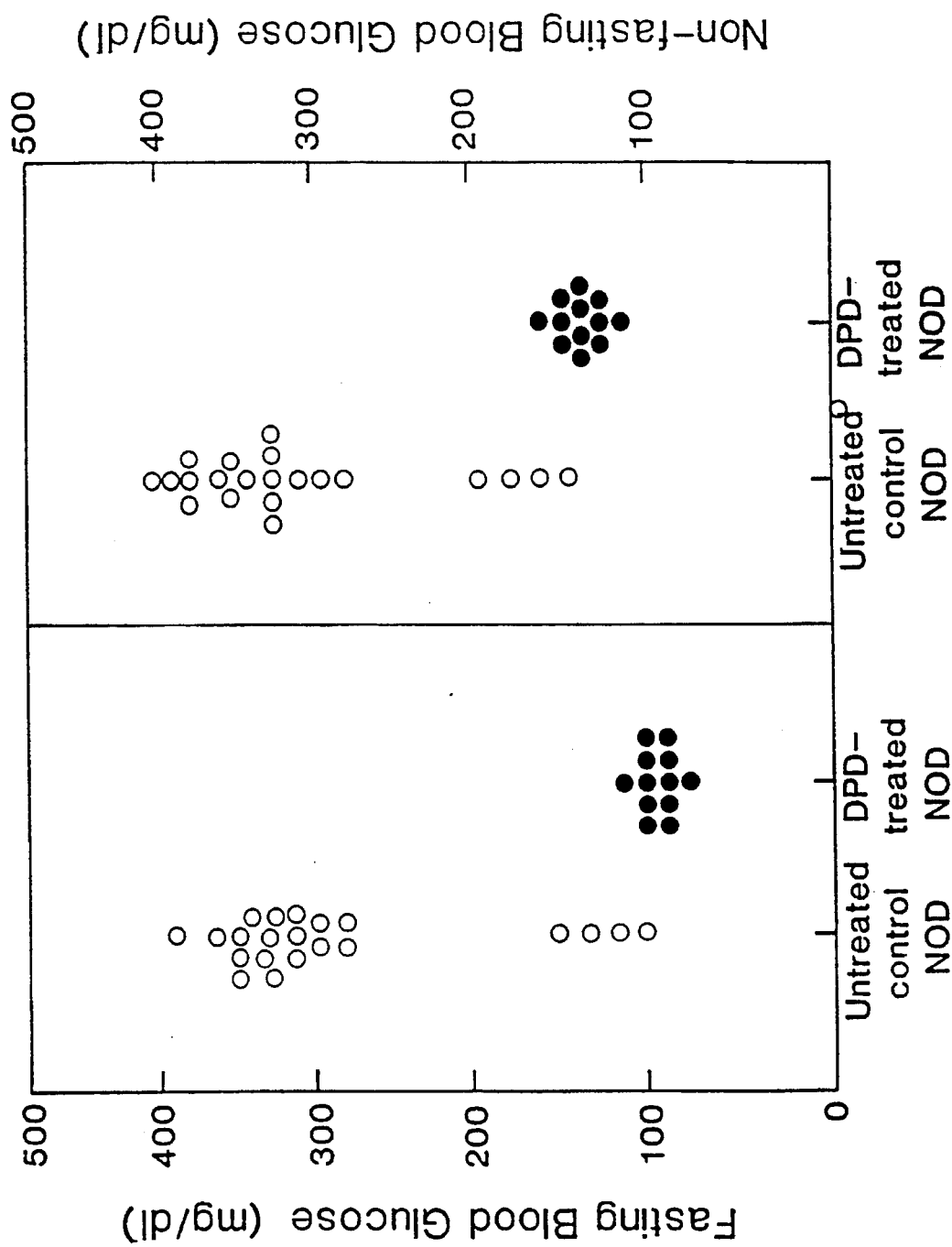
FIG. 2 illustrates that DPD treatment prevents clinical diabetes in NOD mice as evidenced by blood glucose values

NOD mice were dosed with maltol to evaluate its effect on the pathogenesis of type I diabetes. Mice received 5 mg maltol/mouse every other day from age 2 weeks until they were 20 weeks old. Maltol extracted from ginseng as described in Example 2 was used for the first 10 weeks, then maltol purchased from Sigma Co., St. Louis, MO was used thereafter. The mice were kept until they were 35 weeks old. Urine glucose was measured at 3-day intervals from 10 to 35 weeks of age. Urinary glucose and ketone levels were determined using Diastix and Ketostix reagent slips (Miles, Ontario, Canada). Individual mice were classified as being diabetic on the basis of positive glycosuria[38]. None of these treated animals showed any signs of clinical diabetes (0%). In contrast, 78% of age-matched control mice (22 mice) spontaneously developed autoimmune diabetes. The results of this study are shown in FIG. 1. At 35 weeks of age, fasting (8 hours of fasting) and non-fasting blood glucose levels were measured. Blood was obtained from the retro-orbital venous plexus of fasting and nonfasting NOD mice. Glucose levels were measured enzymatically by the glucose oxidase method with o-dianisidine dihydrochloride as the reactive dye [39-41]. The mean nonfasting blood glucose level of 35 ICR mice (nondiabetic control mice; NOD mice were derived from ICR mice) was 149±27 mg/dl. Any non-fasting mouse with a blood glucose level greater than 230 mg/dl (3 SD above the mean) was scored as diabetic. The mean fasting blood glucose level of 38 ICR mice was 137±28 mg/dl. Any fasting mouse with a blood glucose level greater than 221 mg/dl (3 SD above the mean) was scored as diabetic. In fasting mice, treated non-diabetic mice and untreated diabetic mice showed mean values of blood glucose of 92±17 and 334±47 mg/dL, respectively; in non-fasting mice, treated non-diabetic mice and untreated diabetic mice showed mean values of blood glucose of 132±19 and 342±45 mg/dL, respectively (FIG. 2). These studies showed that maltol can prevent clinical diabetes completely.

EXAMPLE 2

Isolation of 3-Hydroxy-2-methyl-4-pyrone from Ginseng Root

One kilogram of fresh ginseng root was boiled with methanol and concentrated in vacuo to give a syrupy extract. The extract was fractionated by solvent partitioning and by lead acetate precipitation [32]. The extract was dispersed in a small volume of water and partitioned with ether. The ether soluble fraction was extracted using 5% NaOH solution. The alkaline extract was acidified using HCl and then extracted using ethyl acetate. The ethyl acetate phase was washed with water, dried over anhydrous sodium sulfate and concentrated to give 32 gm ether soluble acidic fraction. The fraction (Sgm) was chromatographed on a silica gel column (250 gm) using benzene: acetone (4:1) as eluent. A main component giving a red violet spot by FeCl$_3$ was isolated in a pure state, recrystallized twice from acetone to give fine needles (mp 143° C. C$_6$H$_6$O$_3$). It gives a positive iodoform test, reacted with diazomethane, sublimed completely when it was heated slowly above 120° C. and gave a red violet with FeCl$_3$. The UV-absorption maximum was 277 nm (E; 4300) and was shifted to 322nm (E; 3800) by the addition of alkali solution. Mass spectrum analysis shows a molecular ion at m/e 126. Photon magnetic resonance (PMR) gives six portions:

$$\delta \frac{TMS}{CDCl3} ;$$

2.36 (3H, s) of methyl group, 6.41(1H,d, J=6Hz) and 7.68(1H,d, J=6Hz) of olefinic AX protons and 7.0(1H,br.) of hydroxyl proton [2]. Carbon magnetic resonance (CMR) in pyridine gives six carbon peaks at 14.2, 113.3, 143.3, 149.5, 154.1 and 173.2 ppm (TMS) which are superimposable with the spectrum of maltol. IR spectrum gives several strong absorptions at $V_{OH}$3270, $V_{CH}$3070, $V_{c=o}$1660, $V_{c=c}$1570 which is also superimposable with the spectrum of standard maltol. Analysis found; C, 57.1%, H, 4.87%; C$_6$H$_6$O$_3$ requires C, 57.1%, H, 4.76%.

EXAMPLE 3

Measurement of Insulin Levels in DPD-treated and Untreated NOD Mice

Insulin was extracted from the pancreas of non-obese diabetic (NOD) mouse by known methods [33,34]. Briefly, deep frozen pancreatic tissue (50% of each pancreas) was placed into phosphate buffered saline (PBS) and then extraction solution A (380 ml absolute alcohol, 20 ml H$_2$O, 8 ml concentrated HCl and some drops of alcoholic phenol red) was added. This mixture was homogenized with polytron type PT 10-20-350D in glass tubes (15×125 mm) for 30 seconds in position 5. The homogenized material in the tubes was incubated at 4° C. for 10 hours. At the end of the incubation period, the homogenized material was centrifuged at 800 g for 5 minutes for clarification. The supernatant was saved. The pellet was re-extracted with 1 ml of extraction solution B (356 ml absolute alcohol, 124 ml H$_2$O and 7.5 ml HCl). The pellet in extraction solution B was incubated for 4 hours at 4° C. and then homogenized with a polytron as described above. The homogenized material was centrifuged at 800 g for 5 minutes. The supernatant was pooled with the supernatant from the first extraction. The pooled supernatant was neutralized with concentrated $NH_{4}OH$ (about 10 μl) until the phenol red turned to purple. The neutralized supernatant was precipitated at 4° C. and then centrifuged at 800 g for 5 min. The supernatant, which contains insulin, was used for the measurement of insulin by radioimmunoassay.

The concentration of immunoreactive insulin (IRI) in the pancreas from DPD-treated and untreated NOD mice was measured by radioimmunoassay techniques [42-44] using mouse insulin as a standard. Briefly, the extracted samples from NOD mice were mixed with $I^{25}$-insulin, and anti-insulin antibody. The mixed materials were incubated for 2 hours at room temperature. At the end of the incubation period, anti-guinea pig IgG raised in sheep was added and the mixture was incubated for 30 minutes at room temperature. At the end of the incubation, the samples were centrifuged at 1500 g for 10 minutes. The supernatant was completely removed. The radioactivity of the pellets was measured. The percent of activity was determined by the following formula:

$$\% \text{ activity} = \frac{\text{the counts of standard or samples}}{\text{the count of blank}} \times 100$$

On the basis of % activity in standards, a standard curve was constructed. The concentration of each unknown sample from maltol-treated or untreated NOD pancreas was read on the basis of the standard curve. FIG. 3 shows that the majority of untreated NOD mice have very low insulin levels (less than 10 μg/g pancreas), while the few untreated mice that do not become diabetic have insulin levels over 60 μg/g pancreas. The maltol-treated mice have insulin levels that are similar to the non-diabetic, untreated animals. About 75% of the maltol-treated mice have insulin levels over 80 μg/g pancreas and about 25% have insulin levels between 55–75 μg/g pancreas. Maltol treatment resulted in substantial protection from beta cell destruction as compared to untreated diabetic NOD mice.

EXAMPLE 4

Inhibition of Hydrogen Peroxide Induced Free Radical Production by Maltol

One of the possible mechanisms for the destruction of pancreatic beta cells in autoimmune Type I diabetes is their damage by free radicals and cytokines released from macrophages and T lymphocytes. It is hypothesized that maltol can inhibit the action of these released radicals and thus prevent Type I diabetes. We measured the effect of maltol on the inhibition of free radicals produced by hydrogen peroxide.

Chemiluminescence produced by hydrogen peroxide was measured using a liquid scintillation counter (LKB 1217/1217 Rack Beta) set to the tritium channel. Briefly, luminol (5-amino-2,3-dihydro-1,4-phthalazinedione) was dissolved in dimethylsulfoxide and diluted with Krebs-Ringer bicarbonate buffer (pH 7.4) containing 16 μM Hepes and no glucose. The final concentration of dimethylsulfoxide was 0.06 μl/ml. Under these assay conditions, 3 μM luminol and various amounts of hydrogen peroxide ranging from 5–20μl were mixed with 5 ml of Krebs-Ringer bicarbonate buffer, with or without maltol. Chemiluminescence was measured for a 30 second period beginning at 20 seconds after the addition of hydrogen peroxide. We found that 20 μl of hydrogen peroxide is the optimal dose in our system and used this dosage throughout our experiment.

A concentration of 0.2 mM of maltol inhibited the production of free radicals by 60%, as evidenced by the change in chemiluminescence. A concentration of 2 μmM of maltol inhibited 98% of the free radical production and 80 mM of maltol almost completely inhibited the production of free radicals by hydrogen peroxide (99.7%). This indicates that maltol clearly inhibits the production of free radicals (Table 1).

TABLE 1

Inhibition of Hydrogen Peroxide Induced Free Radicals by Maltol

| Concentration of luminol | Amount of $H_2O_2$ | Concentration of Maltol | Chemiluminescence (cpm) | Percent inhibition |
|---|---|---|---|---|
| 3 μM | 20 μl | 0.0 mM | 11845.0 ± 1414.0 | 0 |
| 3 μM | 20 μl | 0.2 mM | 4829.3 ± 792.1 | 60 |
| 3 μM | 20 μl | 2.0 mM | 210. ± 55.1 | 98 |
| 3 μM | 20 μl | 80 mM | 31.6 ± 3.1 | 99.7 |

% shown is the percent of free radical production inhibited by maltol as measured by changes in chemiluminescence.

EXAMPLE 5

Histologic Changes of Pancreatic Islets from DPD-Treated and Untreated NOD Mice

Maltol-treated and untreated NOD mice were sacrificed and 25% of each pancreas was fixed in 6% Formalin. Paraffin-embedded sections were stained with hematoxylin and eosin and examined under an Olympus light microscope [49].

To see whether there are any histological differences between the pancreatic islets of DPD-treated and untreated NOD mice, the pancreatic islets of 35 week old mice were examined with the light microscope after staining with hematoxylin and eosin. These results are presented in Table 2. About 70% of the untreated NOD mice became diabetic and showed beta cell necrosis (present in 64% of examined islets) and severe insulitis (present in 35% of examined islets). In contrast, the untreated mice that did not become diabetic showed significantly less beta cell necrosis (present in 20% of examined islets). The rest of their islets were rated as having either severe (22%), moderate (27%), mild (25%) or no (6%) insulitis. With regard to the DPD-treated NOD mice, approximately 14% of the examined pancreatic islets showed severe beta cell necrosis and about 19% showed severe insulitis. In addition, there were histopathological changes in their pancreatic islets that were rated as moderate (22% of examined islets), mild (30%) or as having no insulitis (15%).

On the basis of these observations, we conclude that maltol-treated NOD mice show much less lymphocytic infiltration of the pancreatic islets as compared to untreated diabetic mice. In addition, untreated non-diabetic NOD mice showed histopathological changes of the islets that are slightly more severe than maltol-treated non-diabetic animals. At the present time, however, it is not known if the lymphocytes found in the pancreatic islets contribute to the destruction of the beta cells, as other studies have shown that some T lymphocytes associated with islets appear to have a protective effect.

Different sub-populations of T-cells (CD4+) are involved in the pathogenesis of IDDM in NOD mice. A CD4+islet-specific T-cell clone derived from NOD mice can accelerate the autoimmune process that leads to diabetes in young NOD mice [50-52]. In contrast, the injection of autoreactive T-cells, isolated as a T-cell line from NOD islets, into young non-diabetic NOD mice profoundly inhibited the development of diabetes. Therefore, islets of diabetic NOD mice apparently contain both effector cells and cells capable of inhibiting these effector cells, which impedes beta cell destruction, or enhancing effector cells, which promotes beta cell destruction [52,53].

overnight at 4° C. in the dark. The slides were then washed in three changes of cold PBS for a total of 20 min to remove any unattached antibody, mounted with Elvanol and observed with an Olympus fluorescence microscope [45].

As it is difficult to determine whether the lymphocytes observed in the pancreatic islets are contributing to beta cell destruction, another method was used to determine whether beta cells from maltol-treated or untreated NOD mice were

TABLE 2

Histological changes of pancreatic islets from DPD-treated and untreated NOD mice.

| DPD Treatment | Diabetes | Animal Number | Beta Cell Necrosis | Severe Insulitis | Moderate Insulitis | Mild Insulitis | Intact Islet |
|---|---|---|---|---|---|---|---|
| + | − | 1 | 5/31 (16) | 6/31 (19) | 7/31 (23) | 9/31 (29) | 4/31 (19) |
| + | −, | 2 | 5/32 (16) | 6/32 (19) | 8/32 (25) | 8/32 (25) | 5/32 (15) |
| + | − | 3 | 3/28 (11) | 5/28 (18) | 5/28 (18) | 11/28 (39) | 4/28 (14) |
| + | − | 4 | 5/31 (16) | 6/31 (19) | 6/31 (19) | 10/31 (33) | 4/31 (13) |
| + | − | 5 | 4/32 (13) | 6/32 (19) | 8/32 (25) | 9/32 (28) | 5/32 (15) |
| − | + | 1 | 18/30 (60) | 12/30 (40) | 0/30 (0) | 0/30 (0) | 0/30 (0) |
| − | + | 2 | 19/31 (61) | 12/31 (39) | 0/31 (0) | 0/31 (0) | 0/31 (0) |
| − | + | 3 | 20/32 (62) | 10/32 (31) | 2/32 (7) | 0/32 (0) | 0/32 (0) |
| − | + | 4 | 21/31 (68) | 9/31 (29) | 1/31 (3) | 0/31 (0) | 0/31 (0) |
| − | + | 5 | 22/32 (69) | 10/32 (31) | 0/32 (0) | 0/32 (0) | 0/32 (0) |
| − | + | 6 | 19/30 (63) | 11/30 (37) | 0/30 (0) | 0/30 (0) | 0/30 (0) |
| − | + | 7 | 20/32 (62) | 12/32 (38) | 0/32 (0) | 0/32 (0) | 0/32 (0) |
| − | − | 1 | 6/31 (19) | 7/31 (23) | 9/31 (29) | 7/31 (23) | 2/31 (6) |
| − | − | 2 | 7/34 (21) | 7/34 (21) | 9/34 (26) | 10/34 (29) | 1/34 (3) |
| − | − | 3 | 6/31 (19) | 7/31 (22) | 8/31 (26) | 7/31 (23) | 3/31 (10) |

"+" indicates "yes" and "−" indicates "no".
Numbers in parenthesis indicate percent. Numbers in denominator indicate number of islets examined.

EXAMPLE 6

Destruction of Pancreatic Beta Cells in DPD-Treated ann Untreated NOD Mice

Fluorescein isothiocyanate-labelled anti-insulin antibody was prepared as described previously 45. Briefly, gamma globulin that was prepared by immunizing guinea pigs with glutaraldehyde polymerized porcine insulin and purified by Sephadex G-200 chromatography was purchased from Index Corp., Glenwood, Ill, USA. This material was labelled with FITC. Unconjugated FITC was removed by dialysis against 0.01M PBS (pH 7.5) and by gel filtration through a Sephadex G-25. The labelled gamma globulin was subsequently absorbed with acetone-treated mouse liver powder to eliminate nonspecific fluorescence. Pancreatic sections (from 25% of each pancreas) prepared from maltol-treated and untreated NOD mice were stained with FITC-labelled anti-insulin antibody and examined under a fluorescent microscope as described elsewhere 47.48. Briefly, pancreatic sections on the slides were flooded with FITC-labelled anti-insulin antibody and incubated in a humidity chamber destroyed or not. Sections of pancreatic islets were stained with a fluorescein-labelled anti-insulin antibody and the number of insulin-containing beta cells in the islets was estimated. Table 3 shows that most of the insulin-containing beta cells were destroyed in the pancreatic islets of untreated, diabetic NOD mice. In contrast, about half of examined islets showed mild beta cell destruction and about 28% of them showed moderate beta cell destruction in untreated, non-diabetic animals. Approximately 22% of the examined islets from the same group of animals showed severe beta cell destruction. In DPD-treated mice, about half of the examined islets (45%) showed mild destruction, 23% showed moderate destruction, 20% showed severe destruction and 12% showed no destruction. Maltol-treated NOD mice showed significantly less destruction of pancreatic beta cells as compared to untreated, diabetic animals.

TABLE 3

Destruction of pancreatic beta cells detected by Fluorescein labelled anti-insulin antibody straining

| DPD Treatment | Diabetes | Animal Number | Destruction of Beta Cells | | | |
|---|---|---|---|---|---|---|
| | | | Severe Destruction | Moderate Destruction | Mild Destruction | Intact |
| + | − | 1 | 3/16 (19) | 4/16 (25) | 7/16 (43) | 2/16 (13) |
| + | − | 2 | 3/17 (18) | 5/17 (29) | 7/17 (41) | 2/17 (12) |
| + | − | 3 | 3/16 (19) | 4/16 (25) | 7/16 (43) | 2/16 (13) |
| + | − | 4 | 4/18 (22) | 3/18 (17) | 9/18 (50) | 2/18 (11) |
| + | − | 5 | 4/19 (21) | 4/19 (21) | 9/19 (47) | 2/19 (11) |
| − | + | 1 | 17/18 (94) | 1/18 (6) | 0/18 (0) | 0/18 (0) |
| − | + | 2 | 18/19 (95) | 1/19 (5) | 0/19 (0) | 0/19 (0) |
| − | + | 3 | 18/18 (100) | 0/18 (0) | 0/18 (0) | 0/18 (0) |
| − | + | 4 | 16/17 (94) | 1/17 (6) | 0/17 (0) | 0/17 (0) |
| − | + | 5 | 15/15 (100) | 0/15 (0) | 0/15 (0) | 0/15 (0) |
| − | − | 1 | 4/17 (23) | 5/17 (29) | 8/17 (48) | 0/17 (0) |
| − | − | 2 | 4/18 (22) | 5/18 (28) | 9/18 (50) | 0/18 (0) |

"+" indicates "yes" and "−" indicates "no".
Numbers in parenthesis indicate percent. Numbers in denominator indicate number of islets examined.
"Severe Destruction" indicates over 70% of beta cell destruction as compared with intact islet.
"Moderate Destruction" indicates 30% to 69% of beta cell destruction in pancreatic islet.
"Mild Destruction" indicates less than 30% of beta cell destruction.
"Intact" indicates no destruction of beta cells.

EXAMPLE 7

Measurement of Glucose Levels in GK Rats Treated Orally with DPD, OSA, DPD and OSA, or PBS To see whether DPD, alone or in combination with other modalities, had any effect on the control of blood glucose levels, GK rats were treated daily from 4 to 14 weeks of age with one of the following:

DPD
OSA
DPD and OSA

At 14 weeks of age, glucose tolerance tests were performed by intraperitoneal injection of 2 mg glucose/gm body weight. Blood glucose levels were determined 60 minutes later using methods previously described[64-67].

Rats receiving DPD alone were intubated daily with a 1.18 % (w/v) solution of DPD in PBS. At 4 weeks of age, rats received 0.5 ml of the 1.18% solution of DPD. This was increased by 0.1 ml/week so that rats at 14 weeks of age received 1.5 ml of the 1.18% solution of DPD. Control rats received the same volume of PBS only.

Rats receiving OSA alone were intubated daily with an aqueous extract of OSA. The extract was prepared by adding 10% dried powdered OSA plant to boiling water, keeping the mixture at the boiling point in a sealed container for 3–4 hours, removing the supernatant, then cooling it for use in intubating the GK rats. This supernatant will be referred to as 10% OSA extract. At 4 weeks of age, rats received 0.5 ml of the 10% OSA extract. This was increased by about 0.15 ml/week so that rats at 14 weeks of age received 2.0 ml of the 10% OSA extract. Control rats received the same volume of PBS.

Rats receiving DPD and OSA were intubated daily with a 10% OSA extract which also contained 1.18% (w/v) DPD. Dose volumes were the same as for rats receiving OSA alone. Control rats received the same volume of PBS.

Results, shown in Table 4, indicate that treatment with DPD caused a mild decrease in blood glucose levels (349±42 mg/dl versus 389±23 mg/dl for controls). OSA treatment also caused a decrease in blood glucose levels (234±41 mg/dl versus 396±21 mg/dl for controls). The most dramatic reduction in blood glucose levels was seen in rats receiving a combination of DPD and OSA (185±41 mg/dl versus 392±27 mg/dl for controls).

These results show that DPD, alone and in combination with other modalities, reduces blood glucose levels in a type II diabetes model. It appears that there is a synergistic effect of DPD and OSA on the control of blood glucose levels. Thus, DPD was shown to be useful for the prevention and treatment of type II diabetes using the GK rat model.

TABLE 4

Effect of treatment with DPD, OSA, and DPD plus OSA on Blood Glucose Levels in NIDDM.

| Treatment | Blood Glucose (mg/dl) |
|---|---|
| DPD | 349 ± 42 |
| PBS Control | 389 ± 23 |
| OSA | 234 ± 41 |
| PBS Control | 396 ± 21 |
| DPD + OSA | 185 ± 41 |
| PBS control | 392 ± 27 |

Modification of the above-described modes of carrying out various embodiments of this invention will be apparent to those skilled in the art following the teachings of this invention as set forth herein. The examples described above are not limiting, but are merely exemplary of this invention, the scope of which is defined by the following claims.

What is claimed is:

1. A method for preventing type II diabetes in a mammal susceptible to developing said diabetes comprising administering to said mammal an effective amount of at least one compound of the formula I:

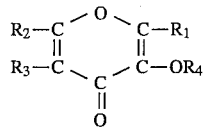

wherein $R_1$, $R_2$ and $R_3$ are independently selected from the group consisting of H, an alkyl of from 1 to 8 carbon atoms, an alkyl-o-alkyl of from 2 to 8 carbon atoms, a haloalkyl of from 1 to 8 carbon atoms and 1 to 3 halogen atoms, an alkenyl of from 2 to 8 carbon atoms with one site of unsaturation, ketones of from 2 to 8 carbon atoms, aldehydes of from 1 to 8 carbon atoms, and any of the above compounds which are alcohol-substituted; and $R_4$ is either H or —$COR_5$, wherein $R_5$ is an alkyl of from 1 to 5 carbon atoms; or a salt thereof.

2. A method according to claim 1 wherein $R_2$, $R_3$, $R_4$, and $R_5$ are each H.

3. A method according to claim 1 wherein said compound is selected from the group consisting of maltol and ethyl maltol.

4. A method for the treatment of type I diabetes in a mammal exhibiting characteristics of said diabetes comprising administering to said mammal an effective amount of at least one compound of the formula I:

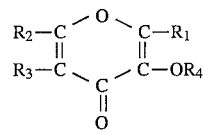

wherein $R_1$, $R_2$ and $R_3$ are selected from the group consisting of H, an alkyl group of from 1 to 8 carbon atoms, an alkyl-o-alkyl from 2 to 8 carbon atoms, a haloalkyl of from 1 to 8 carbon atoms and 1 to 3 halogen atoms, an alkenyl of from 2 to 8 carbon atoms with one site of unsaturation, ketones of from 2 to 8 carbon atoms, aldehydes of from 1 to 8 carbon atoms, and any of the above compounds which are alcohol-substituted; and $R_4$ is either H or —$COR_5$, wherein $R_5$ is an alkyl of from 1 to 5 carbon atoms; or a salt thereof.

5. A method according to claim 4 wherein $R_2$, $R_3$, $R_4$, and $R_5$ are each H.

6. A method according to claim 4 wherein said compound is selected from the group consisting of maltol and ethyl maltol.

7. A method for preventing or treating any diabetes in a mammal in need thereof comprising:

a) administering to said mammal an effective amount of at least one compound of the formula I:

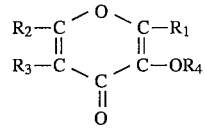

wherein $R_1$, $R_2$ and $R_3$ are selected from the group consisting of H, an alkyl group of from 1 to 8 carbon atoms, an alkyl-o-alkyl from 2 to 8 carbon atoms, a haloalkyl of from 1 to 8 carbon atoms and 1 to 3 halogen atoms, an alkenyl of from 2 to 8 carbon atoms with one site of unsaturation, ketones of from 2 to 8 carbon atoms, aldehydes of from 1 to 8 carbon atoms, and any of the above compounds which are alcohol-substituted; and $R_4$ is either H or —$COR_5$, wherein $R_5$ is an alkyl of from 1 to 5 carbon atoms; or a salt thereof; and b) administering Orthosiphon Aristatus.

8. A method according to claim 7 wherein $R_2$, $R_3$, $R_4$, and $R_5$ are each H.

9. A method according to claim 7 wherein said compound is selected from the group consisting of maltol and ethyl maltol.

* * * * *